United States Patent [19]
Erdrich et al.

[11] Patent Number: 5,708,051
[45] Date of Patent: Jan. 13, 1998

[54] POLYMERIZABLE DENTAL MATERIAL

[75] Inventors: Albert Erdrich, Bad Nauheim; Michael Eck, Schmitten; Kurt Reischl, Merenberg; Slawomira Weber-Pelka, Bad Homburg, all of Germany

[73] Assignee: Heraeus Kulzer GmbH, Hanau, Germany

[21] Appl. No.: 574,522

[22] Filed: Dec. 19, 1995

[30] Foreign Application Priority Data

Dec. 23, 1994 [DE] Germany ............... 44 46 033.3

[51] Int. Cl.$^6$ .............. A61K 6/083; C07C 69/54; C08F 20/18
[52] U.S. Cl. .............. 523/116; 523/115; 523/117; 524/791; 524/456; 524/493; 524/494; 260/998.11
[58] Field of Search .............. 523/115, 116, 523/117; 524/791, 456, 493, 494

[56] References Cited

U.S. PATENT DOCUMENTS

| | | | |
|---|---|---|---|
| 3,066,112 | 11/1962 | Bowen | 523/116 |
| 3,539,533 | 11/1970 | Lee, II et al. | 523/116 |
| 4,029,632 | 6/1977 | Gross et al. | 260/998.11 |
| 4,038,380 | 7/1977 | Cordon | 57/308 |
| 4,141,144 | 2/1979 | Lustgarten | 260/998.11 |
| 4,267,097 | 5/1981 | Michl et al. | 260/998.11 |
| 4,388,069 | 6/1983 | Orlowski | 523/117 |
| 4,389,497 | 6/1983 | Schmitt et al. | 523/116 |
| 4,544,359 | 10/1985 | Waknine et al. | 523/115 |
| 4,581,213 | 4/1986 | Rieck | 423/325 |
| 5,009,597 | 4/1991 | Schaefer | 423/228.1 |
| 5,228,907 | 7/1993 | Eppinger et al. | 106/35 |

FOREIGN PATENT DOCUMENTS

| | | |
|---|---|---|
| 642 780 | 5/1992 | Australia . |
| 0 064 834 B1 | 11/1982 | European Pat. Off. . |
| 0 475 239 A2 | 9/1992 | European Pat. Off. . |
| 24 46 546 | 4/1975 | Germany . |
| 24 03 211 C3 | 7/1975 | Germany . |
| 24 05 578 | 8/1975 | Germany . |
| 34 00 130 A1 | 7/1985 | Germany . |
| 35 32 997 A1 | 4/1986 | Germany . |
| 34 41 564 C2 | 5/1986 | Germany . |
| 37 08 618 C2 | 9/1988 | Germany . |
| 38 26 233 C1 | 10/1989 | Germany . |
| 41 10 612 A1 | 5/1991 | Germany . |
| 41 10 611 A1 | 5/1992 | Germany . |
| 6-237950 | 8/1994 | Japan . |
| 1 408 265 | 10/1975 | United Kingdom . |
| 1 479 329 | 7/1977 | United Kingdom . |
| WO 81/02254 | 8/1981 | WIPO . |

OTHER PUBLICATIONS

Schweiz Monatsschr Zahnmed. vol. 99, Apr. 1989.
Schweiz Monatsschr Zahnmed. vol. 100 8/1990, 953–960.
Derwent Abstract No. 94–312851/39 of JP 06 237 950A.
*Journal of Materials Science*, 17, 3575–92 (1982).

*Primary Examiner*—Andrew E. C. Merriam
*Attorney, Agent, or Firm*—Frishauf, Holtz, Goodman, Langer & Chick, P.C.

[57] ABSTRACT

A dental material that contains di- and poly(meth)acrylates and an inorganic filler in the form of a finely divided synthetic crystalline silicic acid with a sheet structure and optionally a very finely ground glass.

17 Claims, No Drawings

5,708,051

POLYMERIZABLE DENTAL MATERIAL

BACKGROUND OF THE INVENTION

The present invention concerns a polymerizable dental material containing monomeric acrylate, methacrylate or a mixture thereof, a finely divided inorganic filler, and a polymerization catalyst.

The dental material in accordance with the present invention is a composite. It is particularly appropriate for making tooth fillings, crowns, bridges, veneers, inlays, onlays, and artificial teeth and for use as a luting cement.

Polymerizable dental materials for making tooth fillings have been known for many years. The first such materials were mixtures of monomeric and polymeric methyl methacrylate that could be cured inside the patient's mouth in a few minutes, by adding a catalyst or system of catalyst plus accelerator.

The mechanical properties of these materials were improved by adding such finely divided fillers as quartz or aluminum silicates. Their aesthetic properties were improved by developing a catalyst system that did not cause discoloration. Polymerization shrinkage was reduced by using methacrylates of higher alcohols along with or instead of methyl methacrylate.

The first of these new materials was developed by Rafael L. Bowen and disclosed in U.S. Pat. No. 3,066,112. It contains a monomeric binder in the form of a diacrylate or dimethacrylate essentially obtained by reacting a bis-phenol with glycidyl acrylate or methacrylate. It contains an inorganic filler in the form of a finely divided silicon dioxide, preferably silanized. The bis[4-(2-hydroxy-3-methacryloyloxypropoxy)-phenyl]-dimethyl methane ("bis-GMA" or "Bowen monomer") that Bowen discovered is now part of most commercially available dental materials.

Another composite—a dental material that contains a finely divided inorganic filler in addition to organic monomers—is described in U.S. Pat. No. 3,539,533. The polymerizable binder is a mixture of bis-GMA, bis-phenol-A dimethacrylate, a diluting monomer, especially tri-ethylene glycol dimethacrylate, and optionally a small quantity of methacrylate. It is employed with approximately 65 to 75% by weight of the inorganic filler, which can be silicon dioxide, glass, aluminum oxide, or quartz. The inorganic filler can have a particle size of approximately 2 to 85 µm. To improve the bond between the plastic and the filler it can be pretreated with a silane, 3-methacryloyloxypropyl tri-methoxysilane for example.

A material for dental purposes (tooth filling materials, luting cement materials, sealing and protective coating compositions, crown-and-bridge materials, prosthesis materials, and compositions for making artificial teeth) is known for German 2 403 211 C3. It conatins, in addition to a polymerizable acrylate or methacrylate, an inorganic filler in the form of microfine (microdispersed) silicon dioxide with a particle size of approximately 0.01 to 0.4 µm. The polymerizable monomer is bis-GMA or another derivative of bis-phenol A or a reaction product of hydroxy-alkyl methacrylate and di-isocyanates, optionally along with monomeric short-chained methacrylates and/or diacrylates or dimethacrylates. The tooth fillings and similar structures made of the material containing the microfine filler are distinguished by their acceptance of a high-gloss polish and by a translucence similar to that of natural teeth.

Using inorganic fillers in the form of amorphous silicic acid obtained by precipitation or flame hydrolysis and with a maximal particle size of 0.07 µm, optionally mixed with finely divided glass with a maximal particle size of 5 µm along with methacrylates in a dental material that is to be polished to a high gloss is known form German 2 405 578 A1. Bis-GMA, 2,2-bis-[p-(2-hydroxyethoxy)-phenyl]-propane dimethacrylate and triethylene glycol dimethacrylate are named therein as methacrylates.

A dental material containing both conventional and microfine inorganic fillers and accordingly generally disignated hybrid composite is specified in International Patent Application WIPO 81/02 254. It contains a filler in the form of a mixture of hydrophobic silicon dioxide with a diameter of 0.01 to 0.04 µm and glass, x-ray opaque barium or strontium glass for example, with a particle diameter of 2 to 30 µm. The polymerizable monomers are bis-GMA or ethoxylated bis-phenol-A dimethacrylate and triethylene glycol dimethacrylate. This material is employed as a tooth filling material and for veneering cast gold crowns for example.

According to German 3 532 997 A1, composites for dentistry can be manufactured by introducing spherical particles of silicic acid obtained by the ultrasonic vaporization of silica sols into the mixtures appropriate for polymerization. The particles of silicic acid have a diameter between 0.1 and 4 µm and can optionally be modified with a silane coupling agent. The particles can also be combined with other inorganic fillers. The composites are particularly appropriate as crown-and-bridge materials and tooth filling materials instead of amalgam. This composite has special properties. It has good plasticity and is easy to model dental work with, even at filler concentrations higher than 70%. It has less thixotropic action due to the addition of spherical instead of amorphous silicic acid. When irradiated, even work thicker than 2 mm will cure absolutely without sticking. It has the same microhardnesses at both the top and the bottom. It can be polished to a high gloss.

German 3 708 618 C2 and 3 826 233 C2 concern tooth replacement parts with an abrasion-resistant jacket that can be polished to a high gloss. The jacket consists of a plastic containing 10 to 90% by weight of microdispersed silicon dioxide with a particle size of 0.01 to 0.4 µm. The jacket accommodates a core that has high flexural strength and a high modulus of elasticity. The core contains 30 to 90% by weight of an inorganic-filler mixture of 60 to 100% by weight of silicon dioxide, lithium aluminum-silicate glass and/or strontium aluminum-silicate glass with a mean particle size of 0.7 to 5 µm or barium aluminum-silicate glass with a mean particle size of 0.7 to 10 µm and 0 to 40% by weight of microdispersed silicon dioxide with a mean particle size of 0.01 to 0.4 µm. The plastic employed for the core and jacket is preferably a polymer of bis-GMA, ethoxylated bisphenol-A diacrylate or dimethacrylate, triethyleneglycol dimethacrylate, dodecanediol dimethacrylate, diurethane dimethacrylate from 2-hydroxyethyl methacrylate and 2,2,4-trimethylhexamethylene di-isocyanate, bis-(acryloyloxymethyl)-tricyclo-(5.2.1.0$^{2,6}$)decane, and/or bis-(methacryloyloxymethyl)-tricyclo-(5.2.1.0$^{2,6}$)decane. These tooth replacement parts are suitable for supplying crowns, bridges, inlays, and the like.

European 0 475 239 A2 concerns a polymerizable dental material based on an ethylenically unsaturated monomer that contains in addition to a cold-polymerization, hot polymerization, or photopolymerization catalyst, 20 to 90% by weight of an inorganic filler in the form of a mixture of (A) amorphous spherical particles of silicon dioxide and up to 20 mol % of an oxide of at least one element from Groups I, II, III, and IV of the periodic system with an index of refraction of 1.50 to 1.58 and a mean primary-particle size of 0.1 to 1.0 µm and (B) quartz, glass ceramic or glass powder or a mixture thereof with an index of refraction of 1.50 to 1.58 and a mean primary-particle size of 0.5 to 5.0 µm, optionally along with a small quantity of some other fillers to increase opacity and adjust the viscosity. Products made from this material are outstanding for translucence and polishing susceptibility.

A dental material that contains, in addition to monomeric dimethacrylates and an α-diketone/amine system as a photopolymerization catalyst, a filler in the form of a mixture of 80 to 90% by weight of barium aluminum-silicate glass with a mean particle size of 0.5 to 1.5 µm and 10 to 20% by weight of silicon dioxide with a mean particle size of 0.04 to 0.06 µm is known from German 4 110 612 A1. This dental material can be used to make x-ray opaque, abrasion resistant, and high-gloss tooth fillings and inlays.

Dental luting cements are used to bond inlays, onlays, crowns, bridges, and so-called adhesive bridges (Maryland bridges), veneer shells and the like to the tooth substance. Besides cements that harden as a consequence of curing processes, such as the zinc oxide phosphate cements, those that cure by polymerization are also increasingly used. The polymerizable luting cements typically contain esters of acrylic acid or methacrylic acid, as monomeres, and usually contain a fine-grained inorganic filler, along with the catalysts that trigger the polymerization.

An adhesive for bonding objects to teeth is known from European Patent 0 064 834 B1. It contains a resin binder, diluting monomer, at least 20% by weight of inorganic filler, and a polymerization photo-initiator that responds to visible light. The photo-initiator is a mixture of an α-diketon in the form for example of camphorquinone, benzil, biacetyl, 9,10-phenanthrenequinone, naphthoquinone, and an amine, especially a dialkanol or trialkanol amine. The fillers are preferably such inorganic glasses as barium aluminum-silicate glass and lithium aluminum-silicate glass.

The metal surfaces of adhesive bridges can in accordance with German 3 441 564 C2 be bonded securely, tightly, and without any gaps to the dental enamel when the adhesive employed contains not only methacrylates and inorganic filler in the form of silanized silicon dioxide with a particle size of up to 0.04 µm, but also both a chemical cold-polymerization (autopolymerization) catalyst, and a photo-polymerization catalyst.

A low-viscosity) microfilled luting composite cement that is cured in two steps of polymerization is known from the journal Schweiz. Monatsschr. Zahnmed. 99 4 (1989). It is originally yellow and does not attain its final color until completely cured. The cement includes two initiator systems containing a large amount of camphorquinone for the photopolymerization, the absorption maxima of which are at various wavelengths of visible light. The cement is initially cured with light having a wavelength longer than 470 nm and finally cured at wavelengths of approximately 470 nm. Since the cement initially differs in color from the tooth and is of marzipan-like consistency after initial curing, it is easy to manipulate, and any excess can be removed rapidly and reliably without damaging the substance of the tooth.

A similar luting cement that can contain, in addition to the photopolymerization catalyst, a cold-polymerization catalyst is known form German 4 110 611 A1.

BRIEF DESCRIPTION

The object of the present invention is to provide a polymerizable dental material in the form of a paste and containing a monomeric acrylate, methacrylate or a mixture thereof and a finely divided inorganic filler that is appropriate not only for such dental restoration work as tooth fillings, crowns, bridges, veneers, inlays, and artificial teeth but also for bonding dental restoration work and orthodontic devices to the natural teeth and for repairing dental ceramic components. The material is intended as an easy-to-model paste that will retain any shape into which it is modeled during the restoration. The latter property will be called dimensional stability hereinafter. Insufficient dimensional stability is a serious problem in processing and handling conventional dental materials during the dental-technology production of dental restorations. The restorations made from the dental material by dental technology shaping, modeling, and polymerization, are intended to accept a high-gloss polish and to approximate natural teeth with respect to wear and to optical and mechanical properties.

Dental material employed to attain the object of the presend invention is characterized in accordance with the present invention in that it contains an inorganic filler containing 5 to 100% by weight of finely divided synthetic crystalline silicic acid with a sheet structure and 0 to 95% by weight of very finely ground glass. The dental material itself contains 20 to 80% by weight and preferably 40 to 75% by weight of the inorganic filler.

DESCRIPTION OF THE PREFERRED EMBODIMENTS

The dental material according to the presend invention is of the type containing monomeric acrylate, methacrylate or a mixture thereof, a finely divided inorganic filler, and a polymerization catalyst. The improvement provided by the present invention is in the inorganic filler which contains 5 to 100% by weight of finely divided synthetic crystalline silicic acid with a sheet structure and 0 to 95% by weight of very finely ground glass.

One particular proven embodiment of dental material in accordance with the present invention contains 40 to 55% by weight of an inorganic filler composed entirely of finely divided synthetic crystalline silicic acid with a sheet structure. This embodiment is preferred when the dental material is employed as a luting cement.

Another particularly proven embodiment contains 60 to 75% by weight of an inorganic filler consisting of a mixture of 5 to 50 and preferably 10 to 30% by weight of finely divided synthetic crystalline silicic acid with a sheet structure and 50 to 95 and preferably 70 to 90% by weight of very finely ground glass.

It is preferable for the dental material to contain silicic acid with a sheet structure having a particle size distribution form 1 to 40 µm and a mean particle size of approximately 4 µm and glass having a particle size distribution ranging from 0.1 to 5 µm and a mean particle size of approximately 0.7 µm. The silicic acid is a synthetic crystalline silicic acid of the type known for example from German 3 400 130 A1 or the corresponding U.S. Pat. No. 4,581,213, which U.S. patent includes a disclosure of how to make the silicic acid required by the present invention. The silicic acid described and claimed in U.S. Pat. No. 4,581,213 is a synthetic crystalline silicic acid which has a sheet structure and an overall composition $H_2Si_xO_{2x+1}$, wherein x denotes a number between 15 and 24, which exhibits a very strong first line in the X-ray diffraction pattern at $(3.42\pm0.1) \cdot 10^{-8}$ cm and a further line at $(18\pm4) \cdot 10^{-8}$ cm, the intensity of which is not more than 75% of the intensity of the first line, and which has a titratable acidity of 83 to 130 mmol of H+/mol of $SiO_2$.

The particle sizes of the silicic acid and glass are measured with a x-ray diffusion centrifuge. The silicic acid and glass are preferably silanized, by treatment with 3-methacryloyloxypropyl tri-methoxysilane for example.

Especially proven is a dental material containing glass with an index of refraction of 1.46 to 1.53 in mixture with an appropriate choice of the monomeric (meth)acrylate.

The glass is preferably a barium-aluminum borosilicate glass and the (meth)acrylate consists of monomer mixtures with an index of refraction of 1.49 to 1.50 and a viscosity of 1500 to 4000 mPa second at 23° C.

The acrylate and methacrylate appropriate for the monomeric mixtures are the in-themselves known monomeric di- and poly-acrylates and di- and poly-methacrylates: diurethanedi(meth)acrylate of 2,2,4-trimethylhexamethylene di-isocyanate and 2-hydroxyethyl (meth)acrylate, diurethane di(meth)acrylate of bis-(di-isocyanatomethyl)-tricyclodecane and 2-hydroxyethyl (meth)acrylate, decanediol di(meth)acrylate, dodecanediol di(meth)acrylate, tri-ethyleneglycol di(meth)acrylate, bis[4-(2-hydroxy-3-methacryloyloxy propoxy)-phenyl]-dimethyl methane, bis-[4-(2-hydroxy-3-acryloyloxypropoxy)-phenyl]-dimethyl methane, tri(meth)acryloyloxyethoxytrimethylol propane, tetra(meth)acryloyloxyethoxy penta-erythritol, tetra(meth)acryloyloxy-isopropoxy penta-erythritol, and hexa(meth)acryloyloxyethoxy dipenta-erythritol.

It has been demonstrated that a monomeric (meth)acrylate consisting of 5 to 60% by weight of monomeric poly(meth)acrylate has a positive effect on the tooth restoration's abrasion resistance and mechanical properties. Monomeric (meth)acrylate consisting of 30 to 60% by weight of monomeric poly(meth)acrylate is preferred.

The dental material can be cured by hot or cold polymerization as well as by photopolymerization.

Appropriate catalysts are for example organic peroxides like dibenzoyl peroxide for hot polymerization, redox systems, preferably those comprising organic peroxides and amines, for cold polymerization, and ketone-amine systems like those known from GB 1 408 265 B1, camphorquinone and amine for example, for photopolymerization.

It is preferable to cure the dental material by photopolymerization. It will then contain 0.1 to 0.5% by weight and preferably 0.1 to 0.3% by weight of a ketone-amine system. Such amines as N,N-dimethyl-p-toluidine and N,N-bis-(2-hydroxyethyl)-p-toluidine and such esters of 4-dimethylaminobenzoic acid as the ethyl and butoxyethyl esters have been proven especially effective. Preferably 0.02 to 0.1% by weight of a further photo-active component in the form of a benzil acetal can be added to the dental material.

One embodiment of the inventive dental material containing only photopolymerization catalysts has been demonstrated in practice to have a long shelf life as a one-component material in paste form. In another embodiment of the inventive dental material that can be cured additional by cold polymerization, the formulation can be compounded preferably in the form of a two-component material in paste form, whereby it is practical for one paste component to be equivalent to that of the one-component material and the other to contain in addition to the monomeric (meth)acrylate and the inorganic filler, the cold-polymerization catalyst in the form of a peroxide.

The ready-to-use dental material will also contain pigments, anti-oxidants, stabilizers, and other typical additives.

Pyrogenic or precipitated silicic acids are, because of their fineness employed in conventional dental material to render them capable of being polished to a high gloss and to ensure they contain as much filler as possible in accordance with the principle of dense packing. To ensure dimensional stability an attempt must be made to attain a filler content somewhere between flexibility and dryness on the part of the dental materials. They will in that event be very strong, and any cured products made out of them will be hard and brittle because the film of monomer around the particles of filler must be kept very small. If attempts are made along these lines to prepare softer pastes, both the finely divided spherical silicic acid particles and the very finely ground glass particles, which act like spheres, will slip over each other, and any structures or shapes modeled therefrom by the dental technician will tend to run.

Surprisingly, finely divided synthetic crystalline sheet silicic acids with a particle size distribution from 1 to 40 μm (whereby the range for finely divided pyrogenic or precipitated silicic acid is 0.01 to 0.4 μm) lack, due to their macroporous sheet structure and flaky surface morphology, both the rheological and mechanical target conflicts of conventional dental materials. A paste in accordance with the present invention is outstanding for its soft to easy-to-knead and non-stick consistency. It will retain its dimensional stability even throughout extended term modeling procedures. It can be uniformly distributed and stretched out very thin without drying or cracking. It models and molds well and retains its original dimensional stability subsequent to shearing and mechanical stress.

In use, the inventive dental material, after shaping, will maintain the shape and size of a molded form even though it has not yet benn cured by polymerization. Even very fine details will not run. As a luting cement for bonding dental restorations and orthodontic devices to teeth it spreads readily and uniformly throughout the gap between the two surfaces that are to be joined. Excess cement forced out of the gap will not run off, but will harden upon termination of the shearing tension at the site of escape and can easily be removed.

Since dental material in accordance with the present invention needs less filler than conventional materials, more binding polymer can better keep the particles of filler together, making the material more flexible and tougher. The macroporous sheet structure simultaneously allows more silicic acid to penetrate along with the monomer or polymer. The particles of filler will, in contrast to particles ranging in size from 1 to 40 μm and not being homogeneous (with no sheet structure), not affect the acceptance of a high-gloss polish. This means that the dental material in accordance with the present invention does not need as much filler in order to remain dimensionally stable over the long term as well as over the short and can be adjusted to make it easy to model. It also means that tooth restorations made therefrom will be mechanically tough (with high flexural strength and a moderately high modulus of elasticity). They will, surprisingly in spite of the silicic acid's "coarseness", polish to a high gloss.

Tooth restorations made with the dental material will have a mechanical toughness that will result in contact-friction abrasion resistance comparable to that of natural enamel. Due to the high level of polymerization and to the considerable cross-linkage deriving from the monomeric polyacrylates and polymethacrylates, the particles of filler will remain considerably longer at the surfaces of the restorations exposed to wear. The finer hard and rigid particles of glass will be protected during contact wear by the "coarser", polymer-saturated, and resiliently yielding particles of sheet silicic acid.

Polymerization-cured tooth restorations made from a dental material in accordance with the present invention are outstanding for their mechanical toughness, especially with respect to impact toughness, flexural strength and modulus of elasticity approach those of natural teeth. Tooth restorations can be polished to a high gloss. A translucence similar to that of natural teeth can be attained since more than 70% of the transparency of this material, which contains no pigments, will be evident in layers 1 mm thick (as compared to 70–80% for 1 mm of natural enamel). Tooth restorations are aesthetically attractive, are convenient to chew with, and will resist long-term stress.

The dental material in accordance with the present invention is particularly appropriate for tooth fillings, crowns, bridges, veneers, inlays, onlays, and artificial teeth and as a luting cement. It can also be used to repair damaged dental ceramic. It would also be useful for repairing industrial ceramics.

Appropriate monomeric mixtures will now be specified with reference to Examples 1 through 7 and various embodiments of the dental material and of samples made from them with reference to Examples 8 through 15. The properties of the samples are measured and compared with those made from known polymerizable dental material of the composite type (fine hybrid) and from pure ceramic (based on glass and feldspar). The inorganic fillers employed in the embodiments in accordance with the present invention are a finely divided synthetic crystalline sheet silicic acid with a specific surface of 50 to 60 m²/g and an index of refraction of 1.43 and a very finely ground barium-aluminum borosilicate glass consisting of 55% silicon dioxide, 25% barium oxide, 10% aluminum oxide, and 10% boric oxide by weight, with an index of refraction of 1.53.

EXAMPLES 1–7

The seven monomeric mixtures listed in Table I were prepared. Table II indicates their indexes of refraction and viscosities (at 23° C.).

TABLE I

| Example | UEDMA | TCDA | DODDMA | bis-GMA | bis-GA | TMPTEA | PTEA | PTPA |
|---|---|---|---|---|---|---|---|---|
| 1 | 50 |    | 5  | 30 |    | 15 |    |    |
| 2 | 50 | 30 | 5  |    |    |    | 15 |    |
| 3 | 50 |    | 5  |    | 30 |    |    | 15 |
| 4 |    | 70 | 10 |    |    |    | 20 |    |
| 5 |    | 45 |    |    |    |    |    | 55 |
| 6 | 30 |    |    |    | 30 |    | 40 |    |
| 7 | 40 |    |    | 30 |    | 30 |    |    |

All figures % by weight.
UEDMA: diurethanedimethacrylate of 2,2,4-trimethylhexamethylene di-isocyanate and 2-hydroxyethyl methacrylate
TCDA: diurethane dimethacrylate of bis-(di-isocyanatomethyl)-tricyclodecane and 2-hydroxyethyl acrylate
DoDDMA: dodecanediol dimethacrylate
bis-GMA: bis-[4-(2-hydroxy-3-methacryloyloxypropoxy)-phenyl]-dimethyl methane
bis-GA: bis-[4-(2-hydroxy-3-acryloyloxypropoxy)-phenyl]-dimethyl methane
TMPTEA: tri-acryloyloxyethoxytrimethylol propane
PTEA: tetra-acryloyloxyethoxy penta-erythrite
PTPA: tetra-acryloyloxy-isopropoxy penta-erythrite

TABLE II

| Example | Index of Refraction | Viscosity, mPa sec |
|---|---|---|
| 1 | 1.497 | 2500 |
| 2 | 1.490 | 2100 |
| 3 | 1.499 | 2600 |
| 4 | 1.494 | 2900 |
| 5 | 1.491 | 3500 |
| 6 | 1.499 | 2800 |
| 7 | 1.500 | 3200 |

|  | % by weight |
|---|---|
| Example 8 |  |
| A luting cement (composite cement) |  |
| the monomeric mixture from Ex. 2 | 51.68 |
| silicic acid with a sheet structure and a mean particle size of 4 µm | 48.00 |
| phenanthrenequinone | 0.1 |
| N,N-dimethyl-p-toluidine | 0.2 |
| 2,6-di-tert-butyl-4-methylphenol | 0.02 |
| Example 9 |  |
| A luting cement in the form of two pastes curable by photopolymerization and cold polymerization |  |
| Paste A |  |
| the monomeric mixture from Ex. 2 | 53.8 |
| silicic acid with a sheet structure and mean particle size of 4 µm | 45.0 |
| dibenzoyl peroxide | 1.0 |
| 2,6-di-tert-butyl-4-methylphenol | 0.2 |
| Paste B |  |
| the monomeric mixture from Ex. 4 | 49.48 |
| silicic acid with a sheet structure and a mean particle size of 4 µm | 50.00 |
| phenanthrenequinone | 0.2 |
| N,N-dimethyl-p-toluidine | 0.3 |
| 2,6-di-tert-butyl-4-methylphenol | 0.02 |
| Example 10 |  |
| A dental material |  |
| the monomeric mixture from Ex. 1 | 26.58 |

-continued

| | % by weight |
|---|---|
| barium-aluminum borosilicate glass with a mean particle size of 0.7 μm | 58.5 |
| silicic acid with a sheet structure and a mean particle size of 4 μm | 14.5 |
| camphorquinone | 0.1 |
| benzil dimethylacetal | 0.1 |
| N,N-dimethyl-p-toluidine | 0.2 |
| 2,6-di-tert-butyl-4-methylphenol | 0.02 |

Example 11

A dental material

| | |
|---|---|
| the monomeric mixture from Ex. 2 | 27.08 |
| barium-aluminum borosilicate glass with a mean particle size of 0.7 μm | 58.0 |
| silicic acid with a sheet structure and a mean particle size of 4 μm | 14.5 |
| camphorquinone | 0.1 |
| benzil dimethylacetal | 0.1 |
| N,N-dimethyl-p-toluidine | 0.2 |
| 2,6-di-tert-butyl-4-methylphenol | 0.02 |

Example 12

A dental material

| | |
|---|---|
| the monomeric mixture from Ex. 3. | 27.08 |
| barium-aluminum borosilicate glass with a mean particle size of 0.7 μm | 58.0 |
| silicic acid with a sheet structure and a mean particle size of 4 μm | 14.5 |
| camphorquinone | 0.1 |
| benzil dimethylacetal | 0.1 |
| N,N-dimethyl-p-toluidine | 0.2 |
| 2,6-di-tert-butyl-4-methylphenol | 0.02 |

Example 13

A dental material

| | |
|---|---|
| the monomeric mixture from Ex. 4 | 27.08 |
| barium-aluminum borosilicate glass with a mean particle size of 0.7 μm | 58.0 |
| silicic acid with a sheet structure and a mean particle size of 4 μm | 14.5 |
| camphorquinone | 0.1 |
| benzil dimethylacetal | 0.1 |
| N,N-dimethyl-p-toluidine | 0.2 |
| 2,6-di-tert-butyl-4-methylphenol | 0.02 |

Example 14

A dental material

| | |
|---|---|
| the monomeric mixture from Ex. 1 | 27.58 |
| barium-aluminum borosilicate glass with a mean particle size of 0.7 μm | 59.0 |
| silicic acid with a sheet structure and a mean particle size of 4 μm | 13.0 |
| camphorquinone | 0.1 |
| benzil dimethylacetal | 0.1 |
| N,N-dimethyl-p-toluidine | 0.2 |
| 2,6-di-tert-butyl-4-methylphenoi | 0.02 |

Example 15

A dental material

| | |
|---|---|
| the monomeric mixture from Ex. 1 | 28.58 |
| barium-aluminum borosilicate glass with a mean particle size of 0.7 μm | 60.0 |
| silicic acid with a sheet structure and a mean particle size of 4 μm | 11.0 |
| camphorquinone | 0.1 |
| benzil dimethylacetal | 0.1 |
| N,N-dimethyl-p-toluidine | 0.2 |
| 2,6-di-tert-butyl-4-methylphenol | 0.02 |

In these examples, the silicic acid and the barium-aluminum glass are silanized with 3-methacryloyloxyprepyl trimethoxysilane. The benzil dimethylacetal is 1,2-diphenyl-2,2-dimethoxyethanone.

Preparing the Samples

Open metal molds were filled with portions of the dental material from Examples 10 through 15. The materials were irradiated for 180 and 360 seconds in a light-polymerization device (Heraeus Kulzer Dentacolor XS) of the type known for curing photopolymerizable crown-and-bridge materials. The cured samples were evaluated for transparency, abrasion resistance, impact resistance, flexural strength, and modulus of elasticity.

Determining Transparency, Abrasion Resistance, Impact Resistance, Flexural Strength, and Bending Modulus Transparency was determined in accordance with ISO 10 477 with samples 20 mm in diameter and 1 mm thick and a color detector. Color values were obtained over black and white backgrounds and the differences employed as an indication of transparency.

Abrasion resistance was determined by measuring the wear with the mastication simulator described in Schweiz. Montsschr. Zahnmed. 100 (1990), 953–60. The wear was measured in samples 10 mm in diameter and 2 mm thick irradiated for 180 seconds and polished with silicon-carbide paper. A ceramic rod was employed to represent the opposing tooth.

Impact resistance was measured in accordance with DIN 53 453 on samples measuring 15×10×3 mm and flexural strength and modulus of elasticity in accordance with ISO 10 477 on samples measuring 25×2×2 mm with a three-point bending test.

The results for transparency, abrasion resistance, impact resistance, transverse strength, and modulus of elasticity compared with the same parameters for known dental material (fine hybrid and pure ceramic) and with some of the same parameters for enamel and dentin in Table III.

TABLE III

| Sample | Transparency (%) | Abrasion resistance (μm) | Impact resistance KJ/m² | Flexural strength MPa | Modulus of elasticity MPa |
|---|---|---|---|---|---|
| Enamel | 70–80 | 40–60 | — | 10–15 | 80–90 000 |
| Dentin | 60–70 | — | — | 40–60 | 13–18 000 |
| Example 10 | 70 | 70 ± 10 | 2.5 | 120 | 9300 |
| Example 11 | 73 | 50 ± 15 | 2.8 | 120 | 9700 |
| Example 12 | 69 | 60 ± 12 | 3.2 | 125 | 9500 |
| Example 13 | 71 | 45 ± 13 | 3.5 | 135 | 8900 |
| Example 14 | 70 | 60 ± 15 | 2.8 | 134 | 8500 |
| Example 15 | 71 | 55 ± 13 | 3.1 | 110 | 8300 |
| Fine hybrid comparison | 40–50 | 90–120 | 1.5–2.0 | 120–200 | 13–20 000 |
| Pure ceramic comparison | 70–80 | 40–60 | 1–1.5 | 80–120 | 80–120 000 |

Although the invention has been described in considerable detail with particular reference to certain preferred embodiments thereof, variations and modifications can be effected within the spirit and scope of the invention. In particular, it is noted that in this field variation would be obvious especially in view of usual practices in the field.

What is claimed is:

1. In an improved polymerizable dental material of the type containing monomeric (meth)acrylate, a finely divided inorganic filler, and a polymerization catalyst, the improvement wherein the inorganic filler consists essentially of 5 to 100% by weight of finely divided synthetic crystalline silicic acid with a sheet structure and of 0 to 95% by weight of very finely ground glass; wherein the finely divided silicic acid having a sheet structure, has a particle size distribution ranging from 1 to 40 μm and a mean particle size of approximately 4 μm;

the very finely ground glass has a particle size distribution ranging from 0.1 to 5 μm and a mean particle size of approximately 0.7 μm; and the finely divided silicic acid has an overall composition $H_2Si_xO_{2x+1}$, wherein x denotes a number between 15 and 24, which exhibits a very strong first line in the X-ray diffraction pattern at $(3.42\pm0.1)\cdot10^{-8}$ cm and a further line at $(18\pm4)\cdot10^{-8}$ cm, the intensity of which is not more than 75% of the intensity of the first line, and which has a titratable acidity of 83 to 130 mmol of H+/mol of $SiO_2$.

2. The dental material as claimed in claim 1, containing 20 to 80% by weight of the inorganic filler.

3. The dental material as claimed in claim 1, containing 40 to 75% by weight of the inorganic filler.

4. The dental material as claimed in claim 1, containing 40 to 55% by weight of the inorganic filler consisting entirely of finely divided synthetic crystalline silicic acid with a sheet structure.

5. The dental material as claimed in claim 1 containing 60 to 75% by weight of the inorganic filler consisting essentially of a mixture of 5 to 50% by weight of finely divided synthetic crystalline silicic acid with a sheet structure and 50 to 95% by weight of very finely ground glass.

6. The dental material as claimed in claim 5, wherein the mixture consists of 10–30% by weight of finely divided crystalline silicic acid with a sheet structure and 70 to 90% by weight of very finely ground glass.

7. The dental material as claimed in claim 1, containing glass with an index of refraction of 1.46 to 1.53.

8. The dental material as claimed in claim 1, wherein the glass is a barium-aluminum borosilicate glass.

9. The dental material as claimed in claim 1, wherein the finely divided silicic acid and the very finely ground glass have been silanized.

10. The dental material as claimed in claim 9, wherein the monomeric (meth)acrylate is at least one di(meth)acrylate selected from the group consisting of diurethanedi(meth) acrylate of 2, 2, 4-trimethylhexamethylene di-isocyanate and 2-hydroxyethyl(meth)acrylate, diurethane di(meth) acrylate of bis-(di-isocyanatomethyl)-tricyclodecane and 2-hydroxyethyl(meth)acrylate, decanediol di(meth)acrylate, dodecanediol di(meth)acrylate, tri-ethyleneglycol di(meth) acrylate, bis-(4-(2-hydroxy-3-methacryloyloxypropoxy)-phenyl)-dimethyl methane, and bis-(4-(2-hydroxy-3-acryloyloxypropoxy)-phenyl)-dimethyl methane, and at least one polyfunctional (meth)acrylate selected from the group consisting of tri(meth)acryloyloxyethoxytrimethylol propane, tetra(meth)acryloyloxyethoxy penta-erythritol, tetra(meth)acryloyloxy-isopropoxy penta-erythritol, and hexa(meth)acryloyloxyethoxy dipenta-erythritol.

11. The dental material as claimed in claim 10, wherein the monomeric (meth)acrylate consists of 5 to 60% by weight of monomeric poly(meth)acrylate.

12. The dental material as claimed in claim 11, wherein the monomeric (meth)acrylate consists of 30 to 60% by weight of monomeric poly(meth)acrylate.

13. The dental material as claimed in claim 2, wherein the silicic acid and the glass have been silanized and wherein the monomeric (meth)acrylate is at least one di(meth)acrylate selected from the group consisting of diurethanedi(meth) acrylate of 2,2,4-trimethylhexamethylene di-isocyanate and 2-hydroxyethyl(meth)acrylate, diurethane di(meth)acrylate of bis-(di-isocyanatomethyl)-tricyclodecane and 2-hydroxyethyl(meth)acrylate, decanediol di(meth)acrylate, dodecanediol di(meth)acrylate, tri-ethyleneglycol di(meth) acrylate, bis-[4-(2-hydroxy-3-methacryloyloxypropoxy)-phenyl]-dimethyl methane, and bis-[4-(2-hydroxy-3-acryloyloxypropoxy)-phenyl]-dimethyl methane, and at least one polyfunctional meth(acrylate) selcted from the group consisting of tri(meth)acryloyloxyethoxytrimethylol propane, tetra(meth)acryloyloxyethoxy penta-erythritol, tetra(meth)acryloyloxy-isopropoxy penta-erythritol, and hexa(meth)acryloyloxyethoxy dipenta-erythritol and wherein the monomeric (meth)acrylate consists of 5 to 60% by weight of monomeric poly(meth)acrylate.

14. The dental material as claimed in claim 13, wherein the glass is a barium-aluminum borosilicate glass.

15. The dental material as claimed in claim 13 wherein the inorganic filler consists essentially of the silicic acid.

16. The dental material as claimed in claim 13 wherein the inorganic filler consists essentially of 5 to 50% by weight of the silicic acid the remainder being the glass.

17. The dental material as claimed in claim 13 wherein the inorganic filler consists essentially of 5 to 100% of the silicic acid the remainder being the glass.

\* \* \* \* \*